United States Patent [19]

Arakawa et al.

[11] 4,315,914

[45] Feb. 16, 1982

[54] PHARMACEUTICAL COMPOSITIONS USEFUL AS CELLULAR IMMUNOPOTENTIATOR AND ANTITUMOR AGENT AND PROCESS FOR PRODUCTION THEREOF

[75] Inventors: Seiji Arakawa, 2345, Hiyoshi Honcho, Kohoku-Ku, Yokohama-shi, Kanagawa-ken; Tomio Seki, Ohta; Hidekazu Matsuoka, Tokyo; Hatsunori Harada, Suginami; Michinari Ninomiya, Hiroshima, all of Japan

[73] Assignee: Seiji Arakawa, Japan

[21] Appl. No.: 137,502

[22] Filed: Apr. 4, 1980

[51] Int. Cl.³ ............................................ A61K 39/285
[52] U.S. Cl. ...................................... 424/89; 435/235; 435/237
[58] Field of Search ............................ 424/89; 435/237

[56] References Cited

U.S. PATENT DOCUMENTS

| | | | |
|---|---|---|---|
| 2,078,041 | 4/1937 | Terry | 424/89 |
| 2,112,507 | 3/1938 | Sukegawa | 424/89 |
| 2,787,577 | 4/1957 | Allisbaugh | 424/89 |
| 2,879,202 | 3/1959 | Aiston et al. | 424/89 |
| 3,135,661 | 6/1964 | Bartell et al. | 424/89 |
| 3,429,965 | 2/1969 | Selencze et al. | 424/89 |
| 3,985,615 | 10/1976 | Kubo | 424/89 X |
| 4,000,256 | 12/1976 | Hilleman et al. | 424/89 |
| 4,008,317 | 2/1977 | Gits | 424/89 |
| 4,053,582 | 10/1977 | Stickl | 424/89 |
| 4,191,745 | 3/1980 | Mayr et al. | 424/89 X |

FOREIGN PATENT DOCUMENTS

| | | | |
|---|---|---|---|
| 2103519 | 8/1972 | Fed. Rep. of Germany | 424/89 |
| 2328579 | 1/1974 | Fed. Rep. of Germany | 424/89 |
| 270561 | 12/1977 | Fed. Rep. of Germany | 424/89 |
| 43-13888 | 2/1968 | Japan | 424/89 |
| 45-27996 | 9/1970 | Japan | 424/89 |
| 47-22347 | 6/1972 | Japan | 424/89 |

OTHER PUBLICATIONS

Buxton Animal Microbiology, vol. 2 (1977), Blackwell Sci. Pub., p. 409, 414, 420–421, 464–474, 676–710.

*Primary Examiner*—Shep K. Rose
*Attorney, Agent, or Firm*—Larson and Taylor

[57] ABSTRACT

Compositions comprising an attenuated strain of vaccinia virus as active ingredient are found to be useful as cellular immunopotentiator and antitumor agent. The attenuated strain of vaccinia virus is obtained by serial passages of vaccinia virus in cell monolayers of chick embryo cells, preferably after the serial passages in mouse kidney cell monolayers.

10 Claims, No Drawings

PHARMACEUTICAL COMPOSITIONS USEFUL AS CELLULAR IMMUNOPOTENTIATOR AND ANTITUMOR AGENT AND PROCESS FOR PRODUCTION THEREOF

SUMMARY OF THE INVENTION

This invention relates to a pharmaceutical composition of matter useful as cellular immunopotentiator and immune antitumor agent comprising an attenuated strain of vaccinia virus as active ingredient. This invention also relates to a process for the preparation of the composition and to a method of potentiating the immune response in animals and humans by application thereto of the active ingredient, as well as to a method of inhibiting the growth of tumor in animals and humans.

BACKGROUND OF THE INVENTION

Typical examples of microorganisms which are known as antigen to cause certain appreciable cell-mediated immune response in living animals and humans include tubercle bacillus belonging to bacteria and vaccinia virus belonging to viruses. Notice has recently been taken of tubercle bacillus with great interest since BCG vaccine and a cell-wall substance of tubercle bacillus were found to exhibit an immunological antitumor action. However, no extensive use of such antigenic bacteria and the cell materials thereof in clinical applications has yet been made due to side effects associated with them. Attention was once taken about the antitumor action of vaccinia virus. However, the inoculation of an animal body with vaccinia virus generally leads to establishment of a substantial humoral immunity in the living animal body, which, in turn, results in no substantial enhancement of the antitumor effect. For this reason, no great attention has been paid to vaccinia virus in these days.

We have extensively studied in search of an attenuated strain of vaccinia virus which may exhibit a reduced humoral immune activity and an enhanced cellular (cell-mediated) immune activity. As a result, we have now found that when vaccinia virus, either directly or after the serial passages thereof in mouse kidney cell monolayer culture, is serially passed in chick embryo cell monolayer culture, then the virus has been attenuated to such an extent that it has no substantial pock-forming capacity in rabbits but that the attenuated virus possesses both a humoral immune activity reduced to a substantial degree preferably down to substantial naught and a considerably enhanced cell-mediated immune activity in mice, as compared with the original virus. The attenuated strain of vaccinia virus thus obtained has been found to be effective as cellular immunopotentiator and immune antitumor agent.

DETAILED DESCRIPTION OF THE INVENTION

According to a first aspect of this invention, there is provided a pharmaceutical composition of matter useful as cellular immunopotentiator and immune antitumor agent comprising as active ingredient an attenuated strain of vaccinia virus which has no substantial capacity to form pocks in rabbits and which exhibits a substantially reduced humoral immune activity and an enhanced cellular immune activity in mice, in combination with a pharmaceutically acceptable carrier for the active ingredient virus, said attenuated strain having been obtained by the serial passages of vaccinia virus in chick embryo cell monolayer culture, optionally after the serial passages of vaccinia virus in mouse kidney cell monolayer culture.

The attenuated strain of vaccinia virus is preferably one which has a substantially reduced humoral immune activity in mice, as compared to that which the original vaccinia virus possesses.

According to a second aspect of this invention, there is provided a process for the preparation of the pharmaceutical composition of matter as defined hereinabove, which comprises serially passing vaccinia virus in chick embryo cell monolayer culture until the virus has been attenuated to such an extent that it has no substantial pock-forming capacity in rabbits but exhibits a substantially reduced humoral immune activity and an enhanced cellular immune activity in mice, thereby producing an attenuated strain of vaccinia virus, harvesting and purifying the attenuated strain in a manner known in virology, and admixing it with a pharmaceutically acceptable carrier.

In an embodiment of the process of this invention, the serial passages of vaccinia virus in the chick embryo cell monolayer culture, that is, the cell monolayers formed by the in vitro tissue culture of chick embryo cells are preceded by the serial passages of vaccinia virus in the mouse kidney cell monolayer culture, that is, the cell monolayers formed by the in vitro tissue culture of mouse kidney cells. In this embodiment, the virus harvested from the first line of serial passages which were cultured in the mouse kidney cell monolayers is transplanted to the cell monolayer culture of chick embryo cells, where the second line of serial passages of the virus are subsequently carried out.

Examples of vaccinia virus strains which are available for the serial passages of virus to produce the attenuated strain of vaccinia virus according to this invention include Dairen I strain, Lister strain and Ikeda strain of Vaccinia virus which have been stored in National Institute of Health, Japan (see M. Majer and S. A. Plotkin, "Strains of Human Viruses" (1972) pp. 250–253, published from S. Kargel Co., Basel, Paris, London, New York).

The cell monolayers of mouse kidney cells and those of chick embryo cells for use as the culture medium in which such vaccinia virus strain is serially passed, may be prepared under sterile conditions by any conventional technique for the in vitro tissue culture of the respective animal cells. The tissue culture and serial passages of vaccinia virus in the cell monolayer culture may be performed according to a known technique as described in, for example, Alumni Association of National Institute of Health "An Outline of Experimentation on Viruses" 1969, Maruzen Bookstore, Japan; R. C. Parken "Methods of Tissue Culture" 3rd Edition, 1961, Hoeber Co. New York; and J. Paul, "Cell and Tissue Culture" 4th Edition, 1970, Livingstone, London.

It is preferred to carry out the serial passages of virus at a temperature in the range 33° to 37° C. The serial passages are continued until the virus strain subcultivated has substantially lost its pock-forming capacity in rabbits. The pock-forming capacity of the virus strain, if retained therein, can be estimated by a known procedure used conventionally for the preparation of smallpox vaccine. The serial passages of the virus in the mouse kidney cell monolayer culture and in the chick embryo cell monolayer culture may preferably take place over one hundred or more generations and over five or more generations, respectively, depending upon the conditions for the subcultivation to be employed in the particular case.

The attenuated strain of vaccinia virus produced by the serial passages and having a humoral immune activity substantially reduced or preferably substantially lost and a cellular immune activity appreciably increased can be harvested from the cell cultures, purified and formulated into the form of vaccine formulations by any known procedure which is conventionally used for preparation of common virus vaccines. If desired, the attenuated vaccine so obtained may be inactivated by a known virus-inactivation technique, for example, by heating or irradiation with ultraviolet rays.

A typical example of the attenuated strain of vaccinia virus to be used as active ingredient in the composition of this invention is one designated as Vaccinia virus AS strain which can be obtained by the procedure as described in Example 1 hereinbelow and which is deposited under ATCC No. VR-2010 in American Type Culture Collection, U.S.A. (received on Jan. 22, 1980 by ATCC).

In summary, Vaccinia virus AS strain for use in the invention, which is one of viruses belonging to the family vaccinia of the order Poxvirus, has been acquired by serially passing in mouse kidney cell monolayers and in chick embryo cell monolayers the Vaccinia virus Dairen I strain which had been used in Japan until 1947 for the production of smallpox vaccine at the Government Institute for Infections Diseases, University of Tokyo (the predecessor of the present National Institute of Health of Japan and Institute of Medical Science University of Tokyo) and which is disclosed in M. Majer and S. A. Plotkin "Strains of Human Viruses" Page 246 (1972). The passage history of vaccinia virus AS strain comprised the serial passages of the Dairen I strain in mouse kidney cell monolayers at 33° C. over 115 generations and then in chick embryo cell monolayers at 33° C. over 5 generations. For the purpose of cloning (ie. pock-purification) of the virus, the cell culture obtained by the five serial passages in the chick embryo monolayer culture was homogenized and centrifuged at 3,000 r.p.m. for 15 minutes and the supernatant fluid was diluted with phosphate buffered saline (PBS). The virus limited dilution was inoculated to chorioallantoic membranes of 12-day old chick embryos to form a few viral pocks in the membrane. The virus was isolated from a single one of these pocks, and the virus limit dilution was again inoculated to chorioallantoic membranes of 12-day old chick embryos and incubated at 37° C. for 48 hours. Again, the virus was isolated from a single one of the resulting viral pocks, further inoculated at the maximal dilution to chorioallantoic membrances of 12-day old chick embryos and incubated at 37° C. for 48 hours.

The AS strain obtained in this way has the characteristics that it is specifically neutralized with antiserum of Vaccinia virus Dairen I strain, that it is capable of forming smaller and more fine pocks on chorioallantoic membranes of chick embryos, that it is capable of enhancing the cell-mediated immune response in a living animal and that it has lost the neurotropic properties.

The attenuated strain of vaccinia virus according to this invention has no ability to form pocks in humans and rabbits but exhibits a much higher cellular immune activity in mice than that of a known attenuated strain of vaccinia virus and has no neurotropic nature.

The attenuated vaccinia virus for present use which may be either in the form of living virus or in the form of inactivated virus is able to inhibit the growth of malignant tumors. It is well known that the immune response is reduced in tumor-bearing patients. The reduced immune response may be reinstated or potentiated by the administration of an immunologically effective amount of the attenuated vaccinia virus of this invention to these patients.

According to a further aspect of this invention, therefore, there is provided a method of enhancing or potentiating the immune response in a living animal including man, which comprises administering orally or parenterally into the animal an immunologically effective and safe amount of the attenuated strain of vaccinia virus of this invention as defined herein.

The composition of the invention may be formulated for oral or parenteral administration. Compositions in the form of injectable solution may contain a proper titer of the virus as the active ingredient, and also one or more of a pH adjustor, buffer, stabilizer, excipient, and an additive for rendering the solutions isotonic. The injectable solutions may be prepared to be adapted for subcutaneous, intramuscular or intravenous injection by any conventional technique. If desired, the solutions may be lyophilized in a usual manner to prepare lyophilized injections.

Solid compositions for oral administration, which may be in the form of tablets, coated tablets, granules, powders and capsules, may contain excipients for the active ingredients and, if required, other additives including binders, disintegrators, lubricants, colorants, sweetening agents and flavorings.

The dosage of the virus administered will, of course, depend on the mode of administration, the treatment desired and the conditions to be treated. By way of reference, in order to enhance the cellular immune response in mice, the unit dosage generally comprises from 0.001 ml to 0.1 ml of the attenuated virus as the active ingredient having a virus titer of $2\times10^8$ PFU/ml, which may be administered once every day or at one or two day intervals. An optimal dose of the active ingredient in the particular case could easily be determined by routine preliminary experiments known in the art.

According to a more further aspect of this invention, there is provided a method of inhibiting the growth of tumor in a living animal, including man, which comprises administering orally or parenterally into the animal an anti-tumor effective and safe amount of an attenuated strain, either live or inactivated, of vaccinia virus as defined above and particularly of vaccinia virus AS strain identified as ATCC Number VR-2010. According to another aspect of this invention, there is provided a new microorganism, vaccinia virus AS strain (identified as ATCC No. VR-2010) which is an attenuated strain of vaccinia virus which has been obtained by serially passing vaccinia virus Dairen I strain in mouse kidney cell monolayers over 115 generations and subsequently in chick embryo cell monolayers over 5 generations, followed by pock-purification in chick chlorioallantoic membrane in a manner known in virology, and which has no substantial pock-forming capacity in rabbits but with exhibiting a substantially reduced humoral immune activity and an enhanced cellular immune activity in mice.

This invention is further illustrated but not limited by the following Examples.

EXAMPLE 1

This Example illustrates the production of vaccinia virus AS strain which is an attenuated strain of vaccinia virus according to this invention.

(a) Kidneys were excised under sterile conditions from a DDN-strain mouse and washed with Hanks' balanced salt solution (BSS) containing 100 units/ml of penicillin and 100 μg/ml of streptomycin. Then, the kidney cortex was minced into about 3×3 mm square pieces and the pieces obtained from the kidney tissue of one mouse were washed several times with Hanks' BSS to remove the blood as much as possible. The tissue pieces were placed into a digestion flask of 300 ml volume and admixed with 100 ml of Hanks' BSS. The flask was shaken and the supernatant fluid was discarded by suction with a sterile pipette connected to an aspirator, and to the flask was then added fresh 100 ml of Hanks' BSS containing 0.25% trypsin which was previously warmed to 37° C. The mixture was mildly agitated at room temperature for 30 minutes by means of a magnetic stirrer and then allowed to stand to settle the undigested tissue to the bottom of the flask. The cell suspension was pumped into and pooled in a bottle placed in ice water at 4° C. Further 100 ml of Hanks' BSS containing 0.25% trypsin which had been previously warmed to 37° C. was added to the undigested tissue in the flask to effect further digestion as mentioned just above. The digestion was repeated several times.

The total cell suspension which was pooled in said ice-cooled bottle was filtered through a sterilized stainless steel wire cloth of 80 mesh size and then through one of 120 mesh size to remove large cell packets. The filtrate containing dispersed mouse kidney cells was introduced into a centrifuge tube to about one half of the volume of the tube. Into the tube was added Hanks' BSS in a volume of one half of the cell suspension and the mixture was centrifuged at 1,000 r.p.m. for 3 minutes to sediment the cells. The cells were resuspended in a small amount of a growth medium which was made by adding 100 units/ml of penicilline and 100 μg/ml of streptomycin to a mixture of 80 parts by volume of YLE solution (Earle's BSS containing yeast extract and lactalbumin hydrolysate) and 20 parts by volume of ultrafiltrated bovine serum.

The cell suspension thus prepared was estimated for enumeration of the number of cells therein and then diluted with a further amount of said growth medium to a cell concentration of $1 \times 10^5$ to $3 \times 10^5$ cells/ml. The diluted cell suspension was charged in 2 ml portions into test tubes which were sealed, followed by incubation at 37° C. to form cell monolayer of mouse kidney cells. When the cell monolayer was formed, the growth medium was replaced by a fresh maintenance medium having a composition similar to that of the growth medium but containing a lesser amount of the serum.

(b) The mouse kidney cell monolayer was inoculated with a purified sterile suspension of vaccinia virus Dairen I strain at a dose of 0.1 M.O.I. (multiplicity of infection), which was then incubated at 33° C. for 4–6 days. The cultivation was stopped by indication of the cytopathic effect (CPE) developed, and a one-tenth volume of the supernatant of the culture was subjected to the secondary passage that is, to the inoculation and multiplication of virus in the kidney cell monolayer for the second generation. In this way, the serial passages of virus were carried out over 115 generations.

A skin-muscle portion of chick embryo (9 days old) was treated and subjected to the in vitro tissue culture following the procedure similar to that described above for the mouse kidney cells to form the cell monolayer of chick embryo cells on the glass surface of a test tube. The chick embryo cell monolayer was inoculated with the viruses which had been harvested from the serial 115-passages of virus in the monolayer of mouse kidney cells. The serial passages in the chick embryo cell monolayer were effected at 33° C. over 5 generations in the way as mentioned for the serial passages in the monolayer of mouse kidney cells. The cell culture after the 5th passage was homogenized and centrifuged at 3,000 r.p.m. for 15 minutes. The supernatant fluid was obtained as a virus suspension containing the desired attenuated strain of vaccinia virus.

Each of five chorioallantoic membranes of 12-day old chick embryos was inoculated with 0.1 ml of said virus suspension, followed by incubation at 37° C. for further 48 hours, when small pocks were observed on the chorioallantoic membranes. This indicates the viral activity of the virus suspension. Another portion of said virus suspension was taken to determine its virus titer by the tissue culture using chorioallantoic membranes of 12-day old chick embryos. The result was that the virus suspension obtained from the above fifth passage in chick embryo cell monolayer had a virus titer of $2.3 \times 10^6$ PFU (plaque-forming unit)/ml. When 0.1 ml of this virus suspension was intracutaneously injected into rabbits, no local reactions (including formation of pocks) were observed at the injection site.

The virus suspension was inoculated twice onto chorioallantoic membranes of 12-day old chick embryo for cloning of the virus as described hereinbefore. The attenuated strain of vaccinia virus acquired by the above procedure is designated as vaccinia virus AS strain.

(c) The virus suspension obtained in (b) above was purified by Epstein's method using dichlorodifluoroethane (see M. A. Epstein, Brit. J. Exp. Path., 39, 436 (1958)) and then by sucrose gradient centrifugation method (see D. N. Planterose, C. Nishimura and N. P. Salzman, Virology, 18, 294 (1962)) to afford a virus suspension having a titer of $2 \times 10^8$ PFU/ml (hereinafter referred to as AS strain parent suspension).

By way of comparison, chorioallantoic membranes of chick embryos (12 days old) were inoculated with hitherto known viruses, Vaccinia virus M 15 strain (see "Annual Report of National Institute of Health of Japan", Vol. 30, 129 (1976); Vol. 31, 128 (1977) in Japanese), or with Vaccinia virus MVA strain (see H. Stickls and V. Hochstein-Minzel, Münch. Med. Wschr., 113, 1149–1153 (1971) in German). The incubation was made at 37° C. during 4 days for the M 15 strain and at 37° C. during 2 days for the MVA strain. The chorioallantoic membranes on which pocks had developed densely were harvested and homogenized and the homogenate was dispersed in phosphate buffered saline (PBS) to make up a virus suspension, which was then purified by Epstein's method and by sucrose gradient centrifugation method as described hereinabove. There were thus obtained as control specimens M 15 strain parent suspension and MVA strain parent suspension whose virus titers were each adjusted to $2 \times 10^8$ PFU/ml.

EXAMPLE 2

This Example illustrates the pock-forming properties of Vaccinia virus AS strain in rabbits.

The AS strain parent suspension as noted in Example 1 was diluted with varying amounts of PBS to give $10^{-1}$ to $10^{-7}$ dilutions. 0.2 ml of each of the parent suspension and the dilutions was intracutaneously injected into two hair-shaved rabbits weighing about 2 Kg free from the neutralizing antibody against vaccinia virus. Except the rabbits injected with the parent virus suspension, neither swelling nor redness nor induration characteristic of vaccinia virus was observed in the injection sites of the rabbits. It is thus found that the AS strain has no typical ability to form pocks in rabbits.

EXAMPLE 3

This Example illustrates the detection of the IgM antibody-producing capacity of virus by Cunningham method (see A. J. Cunningham, J. B. Smith, E. H. Mercer, J. Exp. Med. 124, 701 (1966)).

0.2 ml of PBS containing 10% sheep red blood cells (SRBC) was intravenously injected into the tail of each DDN-strain SPF (specified-pathogen-free) mouse (5 mice per group). At the same time, each test mouse was intraperitoneally inoculated with 0.1 ml of each of the $10^{-1}$ dilutions of the AS strain parent suspension and the M 15 strain parent suspension as noted in Example 1, and with 0.1 ml of PBS free from virus (as control). 4 Days after the virus inoculation, the mice were sacrificed and the spleens were removed therefrom to examine the plaque-forming cells (PFC). The average number of the plaques counted was $87.4 \pm 65.5$ for groups of mice inoculated with AS strain, $140.8 \pm 33.1$ for those inoculated with M 15 strain and $85.0 \pm 30.1$ for control mice.

In consequence, a significant increase (regarded as significant when $P < 0.05$) in the number of plaques in the spleen is found with the M 15 strain-inoculated mice as compared to the control mice. However, no appreciable difference is observed between the AS strain-inoculated mice and the control mice. This shows that the AS strain leads to no substantial increase in the number of immunocytes of spleen and thus exhibits no substantial humoral immune activity and at least no substantial IgM antibody-producing capacity.

EXAMPLE 4 (a)

This Example illustrates the effect of the AS strain to potentiate the DTH (Delayed-Type Hypersensitivity) response.

0.05 ml of PBS solution containing sheep red blood cells ($10^8$ SRBC/0.05 ml) was injected into the left hind footpad of each ICR-strain SPF mouse (10 mice per group) to establish the sensitization. One week after the first injection of SRBC, the thickness of the right hind footpad of each test mouse was measured with a vernier caliper, and 0.05 ml of PBS solution containing sheep red blood cells ($10^8$ SRBC/0.05 ml) was injected in said right hind footpad (second injection of SRBC for elicitation). Simultaneously with either the first injection of SRBC or the second injection of SRBC, each test mouse was inoculated subcutaneously with 0.1 ml of one of the virus suspensions indicated in Table 1 below wherein the inactivated AS strain $2 \times 10^8$ PFU/ml suspension was such one prepared by heating the AS strain parent suspension at 60° C. for 30 minutes. 24 Hours after the second injection of SRBC, the thickness of the right hind footpad was again measured to estimate the degree of the swelling developed. The swelling degree serves to estimate the delayed-type hypersensitivity response involved.

The test results obtained are set out in Table 1.

TABLE 1

| Virus suspension inoculated | Average increase in thickness of footpad (mm) | |
|---|---|---|
| | Virus Inoculation at first injection | Virus Inoculation at second injection |
| PBS solution (Control) | $0.80 \pm 0.37$ | |
| The inactivated AS strain $2 \times 10^8$ PFU/ml suspension | $1.48 \pm 0.23$* | $0.95 \pm 0.25$ |
| AS strain parent suspension ($2 \times 10^8$ PFU/ml) | $1.52 \pm 0.28$* | $0.98 \pm 0.29$ |
| AS strain $2 \times 10^7$ PFU/ml suspension | $1.45 \pm 0.30$* | $1.04 \pm 0.31$ |
| AS strain $2 \times 10^6$ PFU/ml suspension | $1.40 \pm 0.41$* | $0.84 \pm 0.35$ |
| M 15 strain $2 \times 10^8$ PFU/ml suspension | $0.8 \pm 0.40$ | $0.62 \pm 0.33$ |
| M 15 strain $2 \times 10^7$ PFU/ml suspension | $1.15 \pm 0.29$ | $1.06 \pm 0.14$ |
| M 15 strain $2 \times 10^6$ PFU/ml suspension | $0.9 \pm 0.32$ | $0.96 \pm 0.33$ |

The asterisk (*) indicates a statistically significant difference ($P < 0.05$) as compared with the control value.

The above results show that significantly intensive swelling has been developed only for groups of mice inoculated with the AS strain at the first injection of SRBC (i.e. one week before the second injection of SRBC), thus revealing that the AS strain brings about a considerably improved effect of enhancing or potentiating the cell-mediated immune response over the known M 15 strain. It may be added that the DTH tests as described above is a well known technique which is employed to evaluate the cellular immunopotentiating activity (see Journal of the National Cancer Institute, 51, No. 5, 1669–1675 (1973) and Journal of Experimental Medicine, 139, 528–542 (1974)).

EXAMPLE 4 (b)

Following the same procedure as described in Example 4(a), the tests were conducted using as inoculum the dilutions indicated of the AS strain parent suspension and of the MVA strain parent suspension prepared as in Example 1 in order to evaluate the potentiating effect on the DTH response. The virus inoculation was effected simultaneously with the first injection of SRBC. The test results are set forth in Table 2 below.

TABLE 2

| Virus suspension as inoculum | Average increase in thickness of footpad (mm) |
|---|---|
| PBS solution (Control) | $0.56 \pm 0.25$ |
| MVA strain $10^7$ PFU/ml suspension | $0.75 \pm 0.20$ |
| MVA strain $10^6$ PFU/ml suspension | $0.40 \pm 0.00$ |
| AS strain $10^8$ PFU/ml suspension | $1.41 \pm 0.21$ |
| AS strain $10^7$ PFU/ml suspension | $0.9 \pm 0.15$ |
| AS strain $10^6$ PFU/ml suspension | $0.96 \pm 0.9$ |

As will be seen from Table 2, the AS strain has a greater capacity to potentiate the DTH immune response than that of the MVA strain. Thus, when the AS and MVA strains having the same value of the virus titer for chorioallantoic membranes of chick embryos are compared with each other, it is found that the AS strain which has a reduced pock-forming capacity or non-neurotropic character against rabbits exhibits a higher DTH response-potentiating action and so a higher cellular immune-enhancing activity than the MVA strain.

The following Examples 5-8 illustrate the antitumor effect of the AS strain.

EXAMPLE 5

Groups of ICR-strain SPF mice (female, 5 week old) were intraperitoneally inoculated with 0.1 ml a cell suspension of Sarcoma 180 (titer: $10^2$ cells/0.1 ml). 24 Hours later, they were subcutaneously injected with 0.1 ml of the AS strain $10^6$ PFU/0.1 ml suspension and subsequently with the same dose of the AS strain suspension at two day intervals. 21 Days after the first injection of the virus, all the test mice survived (rate of survival 100%). By way of comparison, only 20% of the control mice untreated with the AS strain survived.

EXAMPLE 6

A cell suspension of Sarcoma 180 ($10^7$ cells/ml) in phosphate buffered saline was inactivated by warming at 60° C. for 30 minutes and 0.1 ml of the tumor cell suspension so inactivated was intraperitoneally injected into groups of ICR-strain SPF mice (5 weeks old) for immunization. One week later, the right foot of each test mouse was subcutaneously inoculated with 0.1 ml of a suspension of living Sarcoma 180 cells ($10^6$ live cells/0.1 ml) in PBS. Immediately after the tumor inoculation, each mouse was subcutaneously inoculated with 0.1 ml of an AS strain $2\times10^7$ PFU/ml suspension or with a $2\times10^7$ PFU/ml suspension of AS strain which was inactivated by heating at 60° C. for 30 minutes, followed by the successive subcutaneous injections of 0.1 ml of the same AS strain suspension at two day intervals. 20 Days after the inoculation with living Sarcoma tumor cells, the mice were sacrificed to remove therefrom the tumors formed. The weight of the tumors was then measured.

The weight of the tumors was $5.47\pm1.89$ g for groups of untreated mice (control), $2.65\pm1.26$ g for groups of mice treated with the live AS strain and $2.57\pm1.38$ g for those treated with the inactivated AS strain. It is thus observed that the AS strain, either live or inactivated, can significantly inhibit the growth of the tumor cells.

EXAMPLE 7

According to Sugimura et al's method (see Experimental Stomach Cancer; Methods in Cancer Research, Vol. 7, pp. 245-308 (1973), Academic Press Co. New York), groups of eight Wistarstrain SPF rats (male, 6 weeks old) were kept in dark while they were allowed to arbitrarily take as the drinking water tap water containing 160 μg/ml of a known carcinogen, MNNG (N-methyl-N'-nitro-N-nitrosoguanidine) and 3.36 mg/ml of Tween 60 ("Tween" is trade name of a surfactant) added thereto. The drinking water was replaced by fresh one two times per week. Each test rat was subcutaneously inoculated with 1 ml of an AS strain $10^7$ PFU/ml suspension or an AS strain $10^6$ PFU/ml suspension just at the beginning of the tests, and subsequently inoculated with 1 ml of the same AS strain suspension at two day intervals to the totally 62 injections of the virus suspension. 218 Days after the first injection of the virus, the rats were dissected to check the polyps developed in the stomachs.

For groups of rats treated with the AS strain $10^7$ PFU/ml suspension, no polyps were observed in the forestomach of five of the eight rats tested but only one or five suspectable polyps were observed in the forestomach of the remaining three rats. The average number of the developed polyps was 0.6 polyps per rat tested. In contrast, for the control groups of untreated rats, 17 polyps per rat were evidently developed on average. For further groups of rats treated with the AS strain $10^6$ PFU/ML suspension, 9.8 polyps per rat were developed on average. With respect to the polyps developed in the glandular stomach of the rats, the average number of the polyps per rat was 2.2 for groups of rats treated with the AS strain $10^6$ PFU/ml suspension, and it was less than 1.5 for those treated with the AS strain $10^7$ PFU/ml. However it was 3.8 for control groups of untreated rats. When these polyps are estimated by histopathological observations, the polyps developed in the groups of rats treated with the AS strain $10^7$ PFU/ml suspension are not regarded as malignant when judged according to WHO Classification (K. Oota and L. H. Sobin, Histological Typing of Gastric and Oesophageal Tumors, International Histological Classification of Tumors, No. 8, W.H.O. Geneva, 1977), whereas none of the polyps developed in the control groups of untreated rats are regarded as benign. The test results clearly indicate the significant antitumor effect of the AS strain.

EXAMPLE 8

Groups of ten CDF-strain SPF mice (female, 8 weeks old) were subcutaneously inoculated with 0.1 ml of a cell suspension of IMC ascites tumor cells ($10^6$ cells/0.1 ml). 24 Hours later, the mice were subcutaneously inoculated at 2 day intervals with 0.1 ml of the AS strain $10^7$ PFU/ml suspension which had been inactivated by irradiation with ultraviolet light. 30 days after the inoculation of the tumor cells, the mice were sacrificed and the weight of the tumors formed was measured to give a mean weight of $9.96\pm6.47$ g. In contrast, the mean weight of the tumors formed was $13.91\pm4.80$ g for the control groups of untreated mice. This distinct difference ($P<0.05$) reveals that administration of the AS strain can inhibits the growth of tumor cells.

EXAMPLE 9

This Example illustrates the non-neurotropic properties of the AS strain.

Groups each consisting of ten DDN-strain mice were inoculated by intracerebral injection of 0.025 ml of the AS strain parent suspension (titer: $2\times10^8$ PFU/ml) or a suspension of Vaccinia virus Dairen I strain (titer: $10^8$ PFU/ml) in PBS, after which one mouse per group was sacrificed every day, and the brain removed from the mouse to make up brain samples of the respective mice according to Coons' method (see A. H. Coons, E. H. Leduc and M. H. Kaplan, J. Exp. Med., 93, 173 (1951)). The brain samples were examined according to the indirect fluorescent antibody technique using an antiserum labelled with fluorescein isothiocyanate. For the groups of mice inoculated with the Dairen I strain, the viruses were detected in all of the brain samples which were prepared on and after the 3rd day after the virus inoculation. While, for those inoculated with the AS strain, no viruses could be detected in all the brain samples which were prepared on the first day to the 8th day after the virus inoculation. These results show that the AS strain has no neurotropic properties.

What we claim is:

1. A pharmaceutical composition of matter useful as cellular immunopotentiator and immune antitumor agent comprising as active ingredient an attenuated strain of vaccinia virus which has no substantial capacity to form pocks in rabbits and which exhibits a substantially reduced humoral immune activity and an enhanced cellular immune activity in mice, in combination with a pharmaceutically acceptable carrier for the active ingredient virus, said attenuated strain having been obtained by the serial passages of vaccinia virus in chick embryo cell monolayer culture, after the serial passages of vaccinia virus in mouse kidney cell monolayer culture.

2. A pharmaceutical composition according to claim 1, in which the attenuated strain of vaccinia virus is Vaccinia virus AS strain (identified as ATCC No. VR-2010) which is either live or inactivated.

3. A process for the preparation of a pharmaceutical composition of matter as defined in claim 1, which comprises serially passing vaccinia virus in mouse kidney cell monolayer culture, then transplanting the mouse kidney cell serially passed vaccinia virus into chick embryo cell monolayer culture and further serially passing the vaccinia virus in chick embryo cell monolayer culture until the virus has been attenuated to such an extent that it has no substantially reduced humoral immune activity and an enhanced cellular immune activity in mice, thereby producing an attenuated strain of vaccinia virus, isolating and purifying the attenuated strain in a manner known in virology, and admixing it with a pharmaceutically acceptable carrier.

4. A process according to claim 3, in which the vaccinia virus to be serially passed is vaccinia virus Dairen I strain.

5. A process according to claim 3, in which the virus is serially passed in the monolayer culture of chick embryo cells over five or more generations at a temperature of 33° C.

6. A process according to claim 3, in which the serial passages in the mouse kidney cell monolayer culture are carried out over one hundred or more generations at a temperature of 33° C.

7. A method of potentiating the immune response in a living animal including man, which comprises administering orally or parenterally into the animal and immunologically effective and safe amount of an attenuated strain, either live or inactivated, of vaccinia virus as defined in claim 1.

8. A method according to claim 7, in which a virus suspension of an attenuated strain of vaccinia virus having a virus titer of $2 \times 10^8$ PFU/ml is administered at a dose of 0.001 to 0.1 ml once every day or at one or two day intervals.

9. A method of inhibiting the growth of tumor in a living animal, including man, which comprises administering orally or parenterally into the animal an antitimor effective and safe amount of an attenuated strain, either live or inactivated of vaccinia virus as defined in claim 1 and particularly of vaccinia virus AS strain identified as ATCC No. VR-2010.

10. As new microorganism, vaccinia virus AS strain (identified as ATCC No. VR-2010) which is an attenuated strain of vaccinia virus which has been obtained by serially passing vaccinia virus Dairen-I strain in mouse kidney cell monolayers over 115 generations and subsequently in chick embryo cell monlayers over 5 generations, followed by pock-purification in chick chorioallantoic membrane in a manner known in virology, and which has no substantial pock-forming capacity in rabbits but with exhibiting a substantially reduced humoral immune activity and an enhanced cellular immune activity in mice.

* * * * *